United States Patent [19]

Gray et al.

[11] 4,361,400

[45] Nov. 30, 1982

[54] FLUIDIC ASSEMBLY FOR AN ULTRA-HIGH-SPEED CHROMOSOME FLOW SORTER

[75] Inventors: Joe W. Gray; Terry W. Alger; David E. Lord, all of Livermore, Calif.

[73] Assignee: The United States of America as represented by the United States Department of Energy, Washington, D.C.

[21] Appl. No.: 210,487

[22] Filed: Nov. 26, 1980

[51] Int. Cl.³ .............................................. G01P 3/40
[52] U.S. Cl. ..................................... 356/23; 209/546;
209/551; 209/579; 209/939; 239/4; 239/102;
209/906; 209/638; 209/3.1; 23/230 B
[58] Field of Search ............... 209/546, 551, 579, 576,
209/127-130, 3.1, 3.3, 932, 127 C, 939, 906,
638; 250/222 PC; 239/4, 102, 290; 358/107;
235/92 PC; 324/71, 71 CP; 23/230 B; 356/39,
23

[56] References Cited

U.S. PATENT DOCUMENTS

| | | | |
|---|---|---|---|
| 3,960,449 | 6/1976 | Carleton | 356/340 |
| 3,970,249 | 7/1976 | Singer | 239/102 |
| 4,043,507 | 8/1977 | Wace | 239/102 |
| 4,230,558 | 10/1980 | Fulwyler | 209/3.1 |

FOREIGN PATENT DOCUMENTS 2748564  9/1978  Fed. Rep. of Germany ........ 356/73

Primary Examiner—Allen N. Knowles

[57] ABSTRACT

A fluidic assembly for an ultra-high-speed chromosome flow sorter using a fluid drive system, a nozzle with an orifice having a small ratio of length to diameter, and mechanism for vibrating the nozzle along its axis at high frequencies. The orifice is provided with a sharp edge at its inlet, and a conical section at its outlet for a transition from a short cylindrical aperture of small length to diameter ratio to free space. Sample and sheath fluids in separate low pressure reservoirs are transferred into separate high pressure buffer reservoirs through a valve arrangement which first permit the fluids to be loaded into the buffer reservoirs under low pressure. Once loaded, the buffer reservoirs are subjected to high pressure and valves are operated to permit the buffer reservoirs to be emptied through the nozzle under high pressure. A sensor and decision logic is positioned at the exit of the nozzle, and a charging pulse is applied to the jet when a particle reaches a position further downstream where the droplets are formed. In order to adjust the timing of charge pulses, the distance between the sensing station at the outlet of the nozzle and the droplet breakoff point is determined by stroboscopic illumination of the droplet breakoff region using a laser and a revolving lucite cylinder, and a beam on/off modulator. The breakoff point in the region thus illuminated may then be viewed, using a television monitor.

10 Claims, 4 Drawing Figures

FLUIDIC ASSEMBLY FOR AN ULTRA-HIGH-SPEED CHROMOSOME FLOW SORTER

ORIGIN OF THE INVENTION

The invention described herein resulted from Contract No. W-7405-ENG-48 between the U.S. Department of Energy and the University of California.

BACKGROUND OF THE INVENTION

The invention relates to an apparatus and method for sorting minute particles in a suspension fluid and more particularly to the fluid system for ultra high speed flow sorting. An example is an ultra-high-speed chromosome flow sorter.

There are many applications for apparatus capable of sorting minute particles entrained in a jet of a suspension fluid. Typically, the jet breaks up into droplets soon after emerging from the jet nozzle with only one particle in a droplet, and preferably only one particle in one out of 10 to 30 droplets to assure at most one particle per droplet. The criterion for sorting may be any particle characteristic that can be sensed in the jet before it breaks off into droplets. Once the characteristic of interest is sensed as a particle passes a sensing station, a decision is made to sort the droplet that will form with that particle. The sorting is accomplished by charging the droplet as it breaks off from the jet. Deflection plates down stream then cause the charged droplet to be deflected into a separate container. One important use of such a flow sorter is in the field of flow cytometry.

Flow cytometry has developed over the last two or three decades to automate counting body tissue cells in an aqueous suspension. Usually the cells have been stained to label the cellular component(s) of interest for quantitative analysis and interpretation. Briefly, the stained cells in the aqueous suspension are caused to flow under low pressure of about 10 psi through an optical sensing station. Once a particle has been sensed it can be counted and/or sorted. Typical sensing rates are 1000 cells per second, but to insure that each charged droplet contain only one cell, it is necessary to produce about 30 droplets for every cell flowing past the sensing station. Consequently, the typical droplet-production rate is $3 \times 10^4$ per second.

It would be desirable to increase the sorting rate by a factor of 10 to 50. The rate of electro-optic or other sensing could be increased by that much since photosensitive and electronic components are available for operation at pulse rates of from $10^6$ to $10^9$ per second. The problem is with the fluidic system, and more particularly the jet velocity at 10 psi and the droplet production rate of $3 \times 10^4$ per second are limiting factors. These have been the limiting factors in flow cytometry and sorting. A higher jet velocity requires a higher operating pressure, which compounds the problem of increasing the droplet rate, and the problem of coordinating the sort decision with the production of a charging pulse.

Although reference has been made to cells, the term has been used by way of example, and not with any intent to limit the invention to sorting only those particles that are the least structural aggregate of living matter capable of functioning as a living unit. The most likely use of this invention is in sorting mammalian chromosomes of a single type for investigations of the biochemical nature and chromosomal specificity of genetic lesions formed as a result of cellular exposure to mutogens or carcinogens. It was discovered at the Lawrence Livermore Laboratory in 1974 that chromosomes could be classified and purified to an unparalleled degree through flow sorting. The procedure is briefly as follows. Fluorescently stained chromosomes are suspended in an aqueous solution which is then surrounded by a sheath fluid in a nozzle so that the chromosomes are ejected one-by-one in a very small jet from an orifice. The chromosomes in the liquid jet pass through an intense laser beam. The resulting fluorescence from each chromosome is sensed and used to make a decision for sorting the droplets produced in response to the ultrasonic vibrations induced by a piezoelectric crystal driven at high frequencies.

OBJECTS AND SUMMARY OF THE INVENTION

An object of this invention is to provide a fluidic assembly for an ultra-high-speed flow sorter which operates about 10 to 50 times faster than existing instruments.

Another object is to provide a flow sorter capable of operating at pressures from about 250 psi to about 1000 psi.

Yet another object is to provide a new and improved jet nozzle which permits laminar flow rates well above the critical Reynolds number above which turbulent flow in a tube is expected.

Still another object is to provide a high intensity system for stroboscopic illumination of the droplet breakoff region to determine the proper position for a charge electrode in a flow sorter, and for the purpose of adjusting the timing of charge pulses following the sensing of a particle to charge droplets to be sorted as they break off from the jet.

These and other objects of the invention are achieved by using a fluid drive system of high pressure in the range of 250 to 1000 psi for greater flow velocity, a nozzle with an orifice having a small ratio of length to diameter for laminar flow rates well above the critical Reynolds number for the high flow velocity, and means for vibrating the nozzle along its axis at high frequencies in a range of about 300 kHz to 800 kHz. The orifice is preferably provided with a sharp edge at its inlet, and a conical section at its outlet for a transition from a short cylindrical aperture of small length to diameter ratio to free space. Sample and sheath fluids in separate low pressure reservoirs are transferred into separate high pressure buffer reservoirs through valve means which first permit the fluids to be loaded into the buffer reservoirs under low pressure and then subjected to high pressure. Once the buffer reservoirs are subjected to high pressure and valve means are operated to permit the buffer reservoirs to be emptied through the nozzle under high pressure, sheathed sample fluid flows through the nozzle and forms a jet at the outlet of the orifice. A piezoelectric crystal at the upper end of the nozzle chamber is driven by a voltage signal at a high frequency. This transmits pulsating forces along the axis of the nozzle to the sheath and sample, which then causes the jet to break up into droplets at the high frequency of the piezoelectric drive signal. However, the droplets are not formed for some finite distance after the jet exits the nozzle orifice. A cytometric sensing station is positioned at the exit of the nozzle, and a charging pulse is applied to the jet when a particle reaches a position further downstream where the droplets are formed so that a droplet containing a particle may be selectively charged as it separates from the jet. Deflection plates even further downstream are then effective to sort out the charged droplets.

In order to adjust the timing of charge pulses to be applied to the jet after sensing a particle to be sorted, the distance between the sensing station at the outlet of the nozzle and the droplet breakoff point is determined by stroboscopic illumination of the droplet breakoff region using a laser beam transmitted through means for breaking up the coherency of the laser beam and means for modulating the beam on and off. The breakoff point in the region thus illuminated may then be viewed, using a television camera and monitor, in order to determine the distance of the droplet breakoff point from the sensing station. Knowing the jet velocity and the distance of this point from the sensing station, the timing of a charging pulse can be so adjusted that it will occur as a particle sensed reaches the droplet breakoff point in order for the droplet formed with the particle to be sorted.

The novel features that are considered characteristic of this invention are set forth with particularity in the appended claims. The invention will best be understood from the following description when read in connection with the accompanying drawings.

Reference will now be made in detail to preferred embodiments of the invention, an example of which is illustrated in the accompanying drawings.

DESCRIPTION OF PREFERRED EMBODIMENTS

Figure 1:
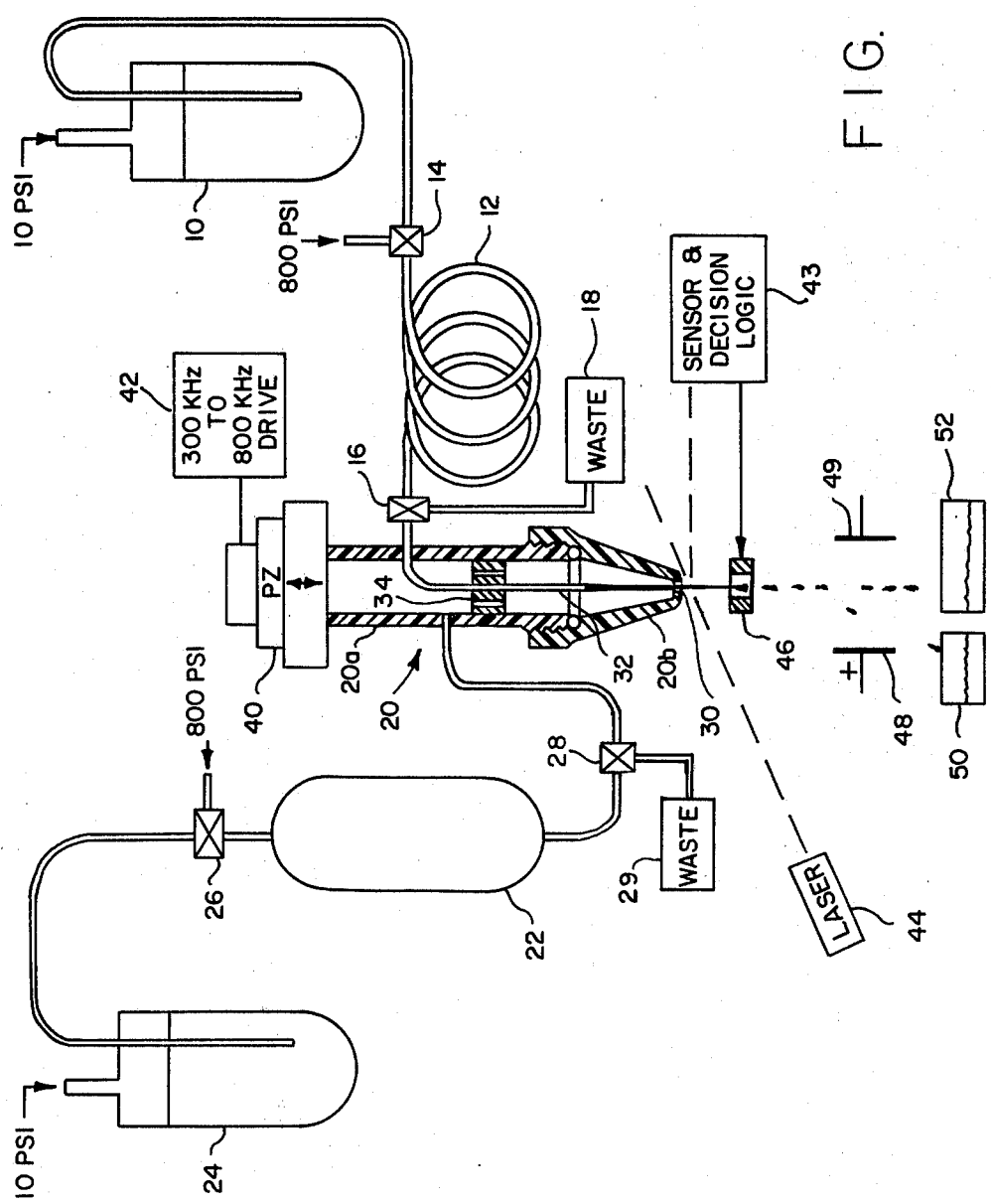
FIG. 1 is a schematic diagram of a cytometer and flow sorter incorporating the novel features of the present invention.

Referring to FIG. 1, an ultra-high-speed flow sorter according to the present invention will now be described with reference to sorting fluid-suspended particles which may be chromosomes in a biological sample. The sample is taken from a vial 10 and transferred into a coil 12 of high-pressure teflon tubing via a two-way valve 14 under low pressure (typically 10 psi) provided by nitrogen, or other inert gas, introduced into the vial 10 from a source (not shown). A second two-way valve 16 connects the output of the sample coil 12 to a waste container 18. Once a portion of the sample flows into this waste container, the low-pressure gas into the vial is cut off, or otherwise removed, leaving the coil filled with a predetermined volume of sample to be run through a nozzle 20. The coil thus serves as a buffer reservoir. In practice, at least one additional sample coil would be provided in order to be able to switch from processing one sample to the other with a minimum of interruption.

Before, or after, loading the sample coil 12 in preparation for a run, a vessel 22 is filled with a sheath fluid from a vial 24, or other container for sheath fluid. To accomplish that, a two-way valve 26 is set for transfer of fluid from the vial 24 under the force of low pressure (typically 10 psi) nitrogen. A two-way valve 28 connects the output of the vessel 22 to a waste container 29, for this transfer operation to allow the vessel 22 to be filled with sheath fluid. Then the low-pressure source of nitrogen is removed from the vial 24. The vessel 22 is thus loaded to function as a buffer reservoir for the sheath fluid.

To process the sample from the coil 12 through an orifice 30 in the nozzle with a sheath of fluid from the vessel 22, the valve 28 is first turned to connect the vessel 22 to the nozzle 20. Then the valve 26 is set to connect a source (not shown) of high-pressure nitrogen, or other inert gas. For purposes of example, the high pressure is illustrated as 800 psi, but may be from about 250 psi to about 1000 psi. This will cause the sheath fluid to fill the nozzle. Once the nozzle is full of sheath fluid, the valve 14 is set to connect the source of high-pressure gas to the coil 12, and the valve 16 is turned to connect the reservoir 12 to the nozzle 20. Sample fluid is thus caused to flow out of a tube 32 in the nozzle.

A spacer 34 holds the tube 32 in alignment with the axis of the nozzle and its orifice 30. Passages in the spacer permit the sheath fluid to flow downwardly, through a cylindrical section 20a and a conical section 20b. This allows the sheath fluid to completely surround the sample fluid as the sample fluid emerges from the tube 32. Both are under about the same high pressure and will flow down through the conical body 20b to the orifice 30 with laminar flow (i.e., nonmixing flow). In practice, the pressure of the sheath fluid is adjusted to be slightly higher than the pressure of the sample fluid to so constrict the diameter of the sample fluid stream as to assure that particles are caused to pass out of the orifice 30 one at a time. Generally, the greater the sheath pressure, the smaller the sample fluid diameter in the nozzle between the output of the tube 32 and the orifice 30 of the nozzle.

The diameter of the nozzle, both in the cylindrical section 20a and the conical section 20b, is so large in comparison to the diameter of the orifice that the flow of sheathed sample may be regarded as being from a very large container of unlimited volume into a small diameter orifice or tube. The orifice is shown enlarged in FIG. 2.

At the orifice, there is an abrupt transition from the relatively large diameter cross section of the conical section 20b to a very small diameter of the orifice 30, typically 0.1 to 4 mils, but the coordination of laminar flow outside and inside the orifice is not disturbed. This is for the reason that the diameter of the orifice is so small that it is like an inlet of a tube connected to a large container of infinite volume, as just noted above. Potential flow theory holds that the inlet is the center for spherical areas of equipotential, represented in FIG. 2 by semicircles. Radius lines eminating from the center of the inlet represent the direction of flow from different spherical areas with equal velocity. As the different spherical areas approach the inlet, they transform into small planar areas of equipotential with a corresponding increase in velocity and with no disturbance in the laminar flow.

This principle of "hydrodynamic focusing" is commonly used in flow cytometers to transform a large stream into a narrow stream, but it has not heretofore been used in flow cytometers at high pressures. Conventional systems operate at about 10 psi. Any significant increase in pressure, such as 300 psi, could not be expected to work stably. This is because, for laminar flow, the Reynolds number, R, must be below a critical value, $R_c$, of 2300. The Reynolds number is given by the fluid flow relationship:

$$R = vd(\rho/\eta)$$

where
  v = average flow velocity
  d = tube diameter,
  $\rho$ = fluid density, and
  $\eta$ = fluid viscosity coefficient.

Figure 2:
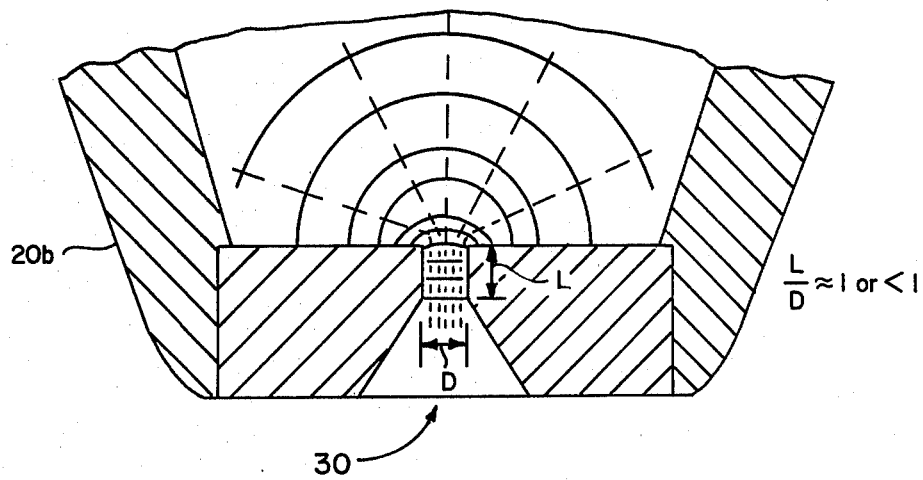
FIG. 2 is an enlarged cross section of the tip of the nozzle in the system of FIG. 1 illustrating the configuration of the nozzle orifice.

For a 70 μm orifice (i.e., d = 70 μm) at an average flow velocity, v, of 80 m/sec, the Reynolds number is typically 5600, well above the critical Reynolds number. Consequently, turbulent flow, and not laminar flow, could be expected, yet turbulent flow has been avoided by the present invention even though the critical Reynolds number is exceeded due to high pressure, which may be as high as from 250 psi to 1000 psi. This has been achieved by maintaining the ratio of the length, L, of the orifice to its diameter, D, small (close to, and preferably less than 1), as shown in FIG. 2 where the length is measured to the end of the constant diameter portion of the orifice 30. Specific examples of nozzles (commercial jewel 51 μm orifices) that have been tested at about 800 psi are as follows:

|   | L/D  | L/D* |
|---|------|------|
| 1 | 0.75 | 1.75 |
| 2 | 2.14 | 2.62 |
| 3 | 0.65 | 1.15 |

*Before grinding down L.

These examples are drastically improved over the same orifices with a larger L/D ratio before grinding, both to reduce L and to provide a sharper inlet corner. And the performances of the first and third samples were superior to the performance of the second. It can therefore be concluded that for the present invention, the L/D ratio should be close to one, not more than about 2, and preferably less than 1. A conical portion of the orifice at the outlet side allows smooth transition from a small diameter to an infinite diameter of free space.

At the outlet of the orifice, a jet is formed of the sample encased in a sheath fluid. The diameter of the sample in the jet is very small, relative to the diameter of the jet, and so small that only one fluid suspended particle will flow out of the nozzle at a time. If the jet is then allowed to break into droplets, any one droplet will not contain more than one particle. A piezoelectric crystal 40 is driven by a high frequency signal (300 kHz to 800 kHz) from a source 42 to form droplets at the high frequency of the drive signal. The ultrasonic vibrations created by the piezoelectric crystal are transferred to the liquid jet through the nozzle 20 and the sheath fluid which fills it. Due to the much higher velocity of the jet stream, higher vibration frequencies can be used to form droplets at a higher rate.

As the jet emerges from the nozzle, and before it breaks up into droplets, the presence of the particle of interest is detected, and the particle detection function of a conventional unit 43, labeled "sensor and decision logic," is used for counting and sorting the detected particles. The type of sensor used depends upon the nature of the particle. There is always some property (electrical, optical or other characteristic) of the particles that allows its detection by a suitable sensor.

Assuming fluorescently stained chromosomes for the particles, the jet is illuminated by an intense beam from a CW laser 44. The resulting fluorescence from each chromosome is sensed and used to select droplets containing the chromosome for sorting by the unit 43. This unit may also contain a counter for determining the number of particles sorted, as will be described with reference to FIG. 4.

Once the presence of a chromosome is detected, the decision logic pulses the jet, either directly through the tube 32, or indirectly through an annular electrode 46 which surrounds the jet. A large negative charge is placed on the droplet then being formed as it breaks off from the jet. The charged droplet is then deflected by plates 48 and 49, thereby causing the chromosome to be collected in a container 50. The unselected droplets (i.e., droplets that are not thus charged) fall into a waste container 52. It can be readily appreciated that the combination of maintaining the fluidic system at a high pressure (exceeding 250 psi), and the jet at a high frequency of vibration (exceeding 300 kHz), provides a sorting rate of $3 \times 10^5$ per second which is ten times higher than the typical rate of $3 \times 10^4$ per second heretofore available. A higher pressure and vibration frequency will produce even higher sorting rates.

In order to adjust the timing of the decision logic 43 to pulse the electrode 46 as a selected droplet is being formed, it is desirable to be able to determine the droplet breakoff point, or more specifically to determine the distance from the sensing station at the exit of the nozzle to the breakoff point, in order that a proper delay may be adjusted in the decision logic for generating the pulse applied to the charging electrode for the particular jet velocity. The pulse applied to the charging electrode may then be synchronized to occur in time coincidence with the formation (breakoff) of a droplet based on the distance to the breakoff point and the velocity of the jet. The velocity, which is a function of pressure for the particular nozzle design, is predetermined, so it is then necessary to determine only the distance. This is usually accomplished by stroboscopic viewing of the droplet breakoff point, using a light emitting diode (LED) and a television camera. However, LED's do not emit sufficient light when operated at high frequencies (above about 250 kHz). Consequently, for the present invention, a laser is used for a strobe light effectively triggered at a 10 kHz to 1 MHz, as shown in FIG. 3.

Figure 3:
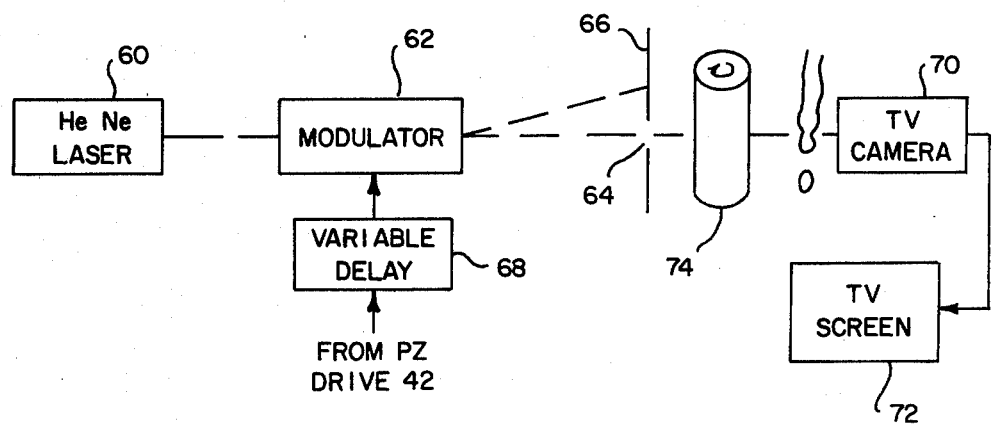
FIG. 3 illustrates schematically a system for stroboscopic illumination of the droplet formation region in the system of FIG. 1 in order to position a charge electrode at the droplet breakoff point and adjust the timing of decision logic for sorting droplets.

Referring now to FIG. 3, a laser (e.g., HeNe laser) 60 is switched by an acousto/optic modulator 62 from a position away from a pinhole 64 in an opaque plate 66 to a position in line with the pinhole. This modulator 62 is comprised of an optically transparent crystal which has a variable periodic optical index of refraction controllable by internally transmitted acoustic waves produced by electrical impulses applied to the crystal. The excitation signal for the modulator is derived from the signal applied to the piezoelectric crystal 40 (FIG. 1) via a variable delay element 68. This variable delay is adjusted to synchronize modulation of the laser beam onto the droplet breakoff region of the jet with droplet formation in order to be able to strobe the formation of droplets as picked up by a television camera 70 and displayed on a television screen 72. A rotating frosted lucite cylinder 74 is placed in the path of the laser beam passed through the pinhole to destroy the coherency of the laser beam and thus avoid speckle that would otherwise occur (due to the coherency of the light) and obscure the droplets on the TV screen.

This arrangement produces a very intense droplet illumination system that operates well even at 800 kHz. The strobe effected in this manner permits stopping the droplets in space as they form. This enables the operator to determine the distance to the breakoff point, and hence the delay to be used in generating a charge pulse at a time which exactly corresponds to the time a droplet having a particle just sensed reaches the droplet breakoff point. In that manner, a particle is sensed in the jet stream and a delayed charge pulse is generated at the moment the particle reaches the droplet breakoff point.

During this procedure for determining the distance of the breakoff point from the sensing station at the outlet of the nozzle, the charge electrode must be removed in order that the television camera view the breakoff point. Consequently, a preferred arrangement for charging the droplets as they break off obviates the need for a charge electrode by applying the charging pulse to the tube 32. For this purpose, the nozzle is made of plastic so that a voltage can be put on the jet for the duration of the pulse. A droplet which then breaks off during the presence of the charging pulse will remain charged throughout its free fall into the container 50. The delayed charging pulse may be produced by the particle detection circuit through a variable monostable vibrator (one-shot circuit) as shown in FIG. 4.

Figure 4:
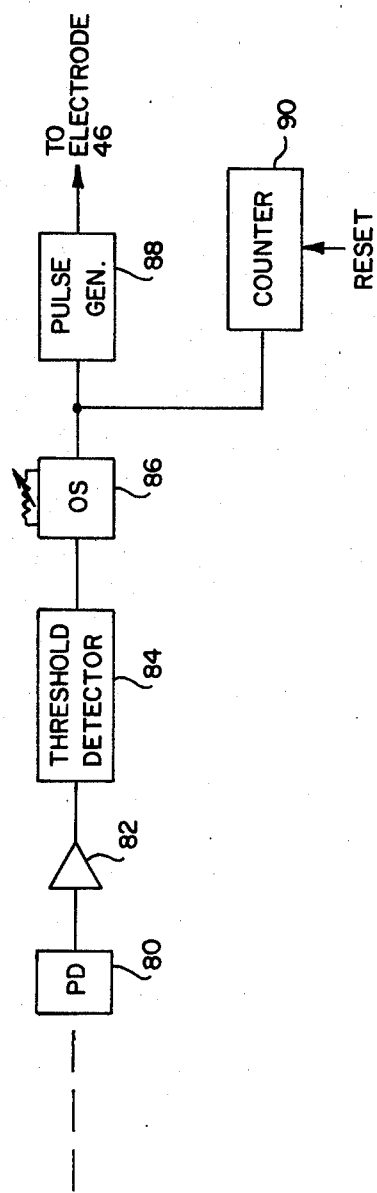
FIG. 4 is a block diagram of an exemplary implementation of a sensor and decision logic for the system of FIG. 1.

Referring now to FIG. 4, an exemplary sensor and decision logic 43 is comprised of: a photodetector 80, amplifier 82, and a threshold detector 84 for the sensing and decision function; and a variable monostable multivibrator (one shot) 86 and a pulse generator 88 for the sorting function. The threshold detector eliminates noise below a predetermined level and allows a signal pulse produced by a sensed particle (via the photodetector 80) to trigger the one shot 86. The trailing edge of the one shot then triggers the pulse generator 88. In this example, the decision to generate a pulse is based solely on the amplitude of a light pulse due to fluorescence of a particle passing through the laser beam. Other characteristics sensed in other ways, and other criteria, could be used in similar or analogous ways for the sensing and decision functions. For each electrode charging pulse generated, a counter 90 is incremented by one in order to have a count of all particles sorted. This counter is reset at the start of each run by applying a rest pulse.

It should now be apparent that an ultra-high-speed flow sorter is provided wherein a sample of particles suspended in a fluid under high pressure in excess of 250 psi is sheathed with a fluid at the same high pressure and expelled as a jet through a nozzle vibrated at high frequency in excess of 300 kHz to form droplets at the rate of nozzle vibration. The average flow velocity of the fluid through the nozzle orifice is so high that the critical Reynolds number for laminar flow is exceeded, yet laminar flow is maintained due to a small length to diameter ratio of the orifice. A pressure buffer between the high pressure part of the system and the low pressure sheath and sample sources facilitates use of very high pressures. In order to adjust the timing of charging pulses for sorting the droplets, a high intensity laser beam is used to illuminate the breakoff region of the droplets, and strobed (modulated) to stop the droplets in space as they break off. To remove laser speckle (due to the coherency of the light) so the droplets can be seen, a rotating frosted lucite cylinder is placed in the beam path which destroys the coherency of the light.

Although particular embodiments have been described and illustrated herein, it is recognized that modifications and equivalents may readily occur to those skilled in the art. Consequently, it is intended that the claims be interpreted to cover such modifications and equivalents.

What is claimed is:

1. In a process for sorting minute particles in a suspension fluid ejected as a jet from a nozzle at high speed, a method of producing droplets from said jet at a high frequency, comprising the steps of providing a nozzle designed for laminar flow of a narrow sample stream and surrounding sheath fluid at high pressure with an orifice having a ratio of length to diameter sufficiently small to maintain laminar flow therethrough of said sample and sheath fluids, and a sharp right angle edge at the inlet thereof to preserve laminar flow during the transition of flow in said nozzle to flow through said orifice at high speed, connecting sheath fluid to said nozzle at high pressure to produce a high velocity jet from the orifice thereof, connecting sample fluid to a tube in said nozzle at the same high pressure as said sheath fluid, said tube being positioned with its outlet aligned with the axis of sheath fluid flow through said orifice to place the sample fluid stream at the center of the jet, and vibrating said nozzle along the axis of said jet at said high frequencies, thereby to cause said jet to break off into droplets at said high frequency.

2. The method as defined in claim 1 wherein said ratio of length to diameter is in a range of about 2 to less than 1.

3. The method as defined in claim 2 wherein said high pressure is in a range from about 250 psi to 1000 psi.

4. The method as defined in claim 3 wherein said high frequency of vibration is in a range from about 300 kHz to about 800 kHz.

5. A method as defined in claim 1, 2, 3 or 4 including a method for observing the breakoff point of said droplets comprised of producing a high intensity laser beam, modulating said beam on and off to strobe the jet and droplet breakoff area at the frequency of vibration and in synchronism with droplet breakoff, and destroying the coherency of said laser beam to have high intensity noncoherent light illuminatethe jet and droplet breakoff area, and producing an enlarged video image of the jet and droplet breakoff area for determining the distance of the droplet breakoff point from a predetermined point near the orifice of said nozzle.

6. In a flow sorter for sorting particles entrained in a suspension fluid ejected as a jet from a nozzle at high speed, a system for producing droplets from said jet at a high frequency comprising, a nozzle designed for laminar flow of a narrow sample stream in a sheath fluid at high pressure, said nozzle having an orifice with a ratio of length to diameter sufficiently small to maintain laminar flow therethrough of said sample and sheath fluids, and further having a sharp right angle edge at the inlet thereof to preserve laminar flow during the transition of flow in said nozzle to flow through said orifice at high speed, high pressure means for introducing said sample and sheath fluids into said nozzle with the sample stream at the center of the flow aligned with the axis of said orifice, and means for vibrating said nozzle along said axis at said high frequency, thereby to cause said jet to break off into droplets at said high frequency.

7. The combination of claim 6 wherein said ratio of length to diameter is in the range of about 2 to less than 1.

8. The combination of claim 7 wherein said pressure is in a range from about 250 psi to 1000 psi.

9. The combination of claim 8 wherein said high frequency of vibration is in a range from about 300 kHz to about 800 kHz.

10. The combination of claim 6, 7, 8 or 9 including means for observing the breakoff point of said droplets comprised of a high intensity laser beam, means for modulating said beam on and off to strobe the jet and droplet breakoff area at the frequency of vibration and in synchronism with droplet breakoff, means for destroying the coherency of said laser beam illuminating said jet and droplet breakoff area, and means for producing an enlarged video image of said jet and droplet breakoff area for determining the distance from a point near said orifice to the droplet breakoff point.

* * * * *